US007017161B1

(12) United States Patent
Cyr et al.

(10) Patent No.: US 7,017,161 B1
(45) Date of Patent: Mar. 21, 2006

(54) SYSTEM AND METHOD FOR INTERFACING A RADIOLOGY INFORMATION SYSTEM TO A CENTRAL DICTATION SYSTEM

(75) Inventors: James Cyr, Clinton, CT (US); Channell Greene, Bridgeport, CT (US); Regina J. Kuhnen, Trumbull, CT (US)

(73) Assignee: Dictaphone Corporation, Stratford, CT (US)

( * ) Notice: Subject to any disclaimer, the term of this patent is extended or adjusted under 35 U.S.C. 154(b) by 0 days.

(21) Appl. No.: 09/415,617

(22) Filed: Oct. 11, 1999

(51) Int. Cl.
G06F 9/00 (2006.01)
(52) U.S. Cl. .................... 719/328; 707/1; 707/3; 707/10; 707/104.1; 705/2; 705/3
(58) Field of Classification Search ............. 719/328; 707/1, 3, 10, 104.1; 705/2, 3
See application file for complete search history.

(56) References Cited

U.S. PATENT DOCUMENTS

| | | |
|---|---|---|
| 3,694,509 A | 9/1972 | Rylander et al. |
| 3,703,445 A | 11/1972 | Tamopol et al. |
| 3,994,000 A | 11/1976 | Trainor et al. |
| 4,319,337 A | 3/1982 | Sander et al. |
| 4,325,777 A | 4/1982 | Yarwood et al. |
| 4,833,625 A | 5/1989 | Fisher et al. |
| 4,837,830 A | 6/1989 | Wrench, Jr. et al. |
| 5,033,077 A | 7/1991 | Bergeron et al. |
| 5,146,439 A | 9/1992 | Jachmann et al. |
| 5,163,085 A | 11/1992 | Sweet et al. |
| 5,216,744 A | 6/1993 | Alleyne et al. |
| 5,265,075 A | 11/1993 | Bergeron et al. |
| 5,294,229 A | 3/1995 | Hartzell et al. |
| 5,398,220 A | 3/1995 | Barker |
| 5,423,034 A | 6/1995 | Cohen-Levy et al. |
| 5,444,768 A | 8/1995 | Lemaire et al. |
| 5,469,353 A * | 11/1995 | Pinsky et al. ............... 382/131 |
| 5,477,511 A | 12/1995 | Englehardt |
| 5,481,645 A | 1/1996 | Bertino et al. |
| 5,491,774 A | 2/1996 | Norris et al. |
| 5,548,566 A | 8/1996 | Barker |
| 5,568,538 A | 10/1996 | Tamir et al. |
| 5,615,112 A | 3/1997 | Liu Sheng et al. |
| 5,625,678 A | 4/1997 | Blomfield-Brown |
| 5,729,734 A | 3/1998 | Parker et al. |
| 5,742,736 A | 4/1998 | Haddock |
| 5,774,841 A | 6/1998 | Salazar et al. |
| 5,799,280 A | 8/1998 | Degen et al. |

(Continued)

OTHER PUBLICATIONS

Cosie, "An Open Medical Imaging Workstation Architecture for Platform-Independent 3-D Medical Image Processing and Visualization", IEEE, Jan. 1997, pp. 279-283.*

(Continued)

*Primary Examiner*—W. Thomson
*Assistant Examiner*—Phuong N. Hoang
(74) *Attorney, Agent, or Firm*—Kelley Drye & Warren LLP

(57) ABSTRACT

A software system provides an interface between a radiology information system and a central dictation system. The software includes first and second application modules which are both in communication with a database management system. Other components of the software system include protocol DLL's (dynamic linked libraries) and a communication DLL. Each of the software components maintains a separate trace buffer. An event occurring in any one of the components triggers a dump of all of the trace buffers. A server socket object is maintained in existence and placed in an accept mode when a client socket terminates communication with the server socket object.

4 Claims, 16 Drawing Sheets

U.S. PATENT DOCUMENTS

| | | | |
|---|---|---|---|
| 5,812,882 A | 9/1998 | Raji et al. | |
| 5,818,800 A | 10/1998 | Barker | |
| 5,839,108 A | 11/1998 | Daberko et al. | |
| 5,898,916 A | 4/1999 | Breslawsky | |
| 5,903,871 A | 5/1999 | Terui et al. | |
| 5,913,061 A | 6/1999 | Gupta et al. | |
| 5,982,857 A | 11/1999 | Brady | |
| 5,986,568 A | 11/1999 | Suzuki et al. | |
| 6,014,440 A | 1/2000 | Melkild et al. | |
| 6,038,199 A | 3/2000 | Pawlowski et al. | |
| 6,094,688 A | 7/2000 | Mellen-Garnett et al. | |
| 6,122,614 A | 9/2000 | Kahn et al. | |
| 6,175,822 B1 | 1/2001 | Jones | |
| 6,263,330 B1 * | 7/2001 | Bessette | 707/4 |
| 6,282,154 B1 | 8/2001 | Webb | |
| 6,308,158 B1 | 10/2001 | Kuhnen et al. | |
| 6,321,129 B1 | 11/2001 | D'Agosto | |
| 6,356,754 B1 | 3/2002 | Onozawa et al. | |
| 6,421,667 B1 * | 7/2002 | Codd et al. | 707/4 |
| 6,434,569 B1 * | 8/2002 | Toshimitsu et al. | 707/100 |
| 6,494,831 B1 * | 12/2002 | Koritzinsky | 600/301 |

OTHER PUBLICATIONS

U.S. Appl. No. 09/190,536, Dwyer et al., Not pub.

Lisa J. Stifleman, Voice Notes: An Application for a Voice-Controlled Hand-Held Computer, MIT Master's Thesis (Jun. 1992).

TechEncyclopedia, Definition of "Download," TechWeb; The Business Technology Network, 2002, 2 pages.

Uploading—a Whatis Definition, Tech Target, 2002, 2 pages.

* cited by examiner

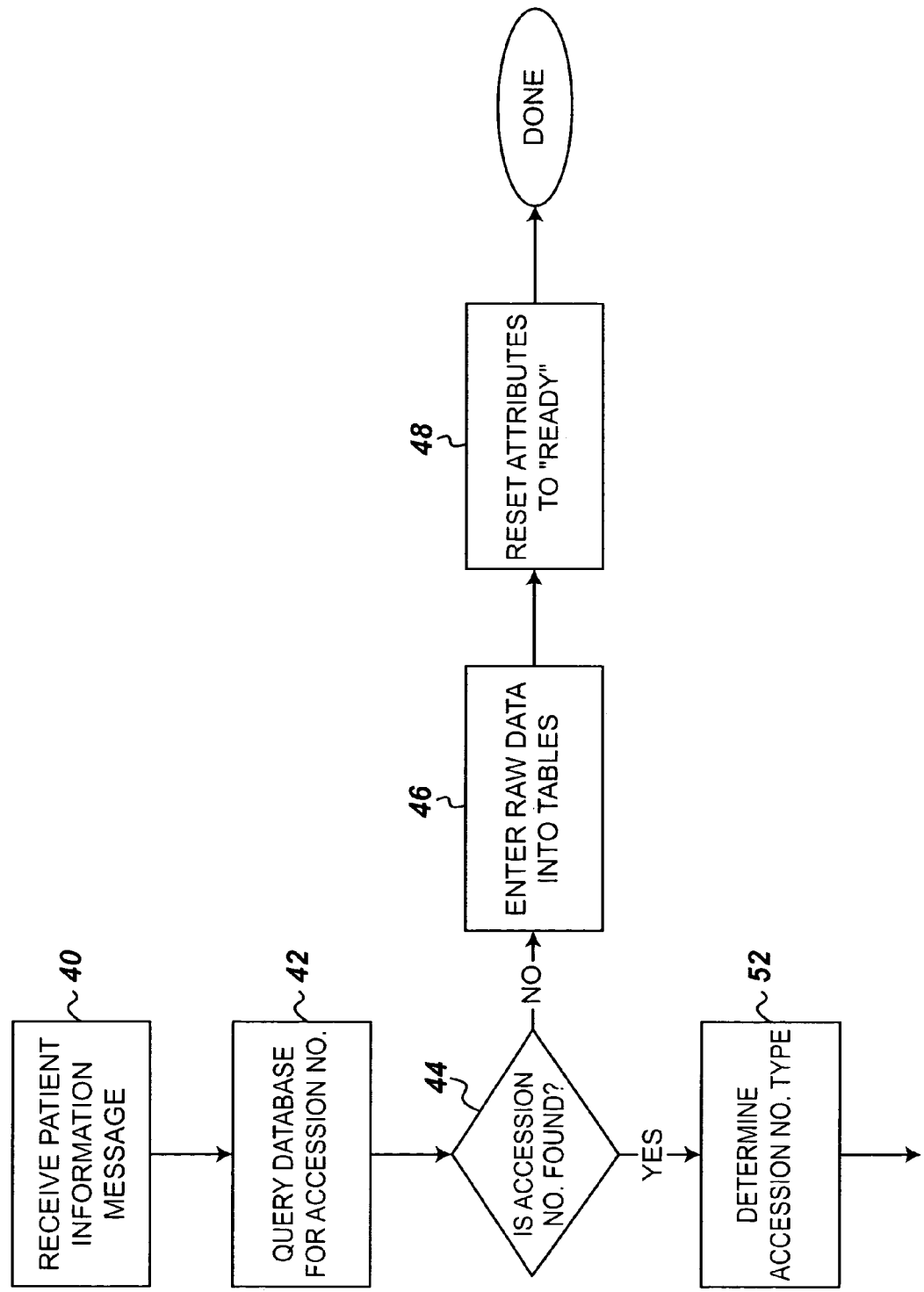

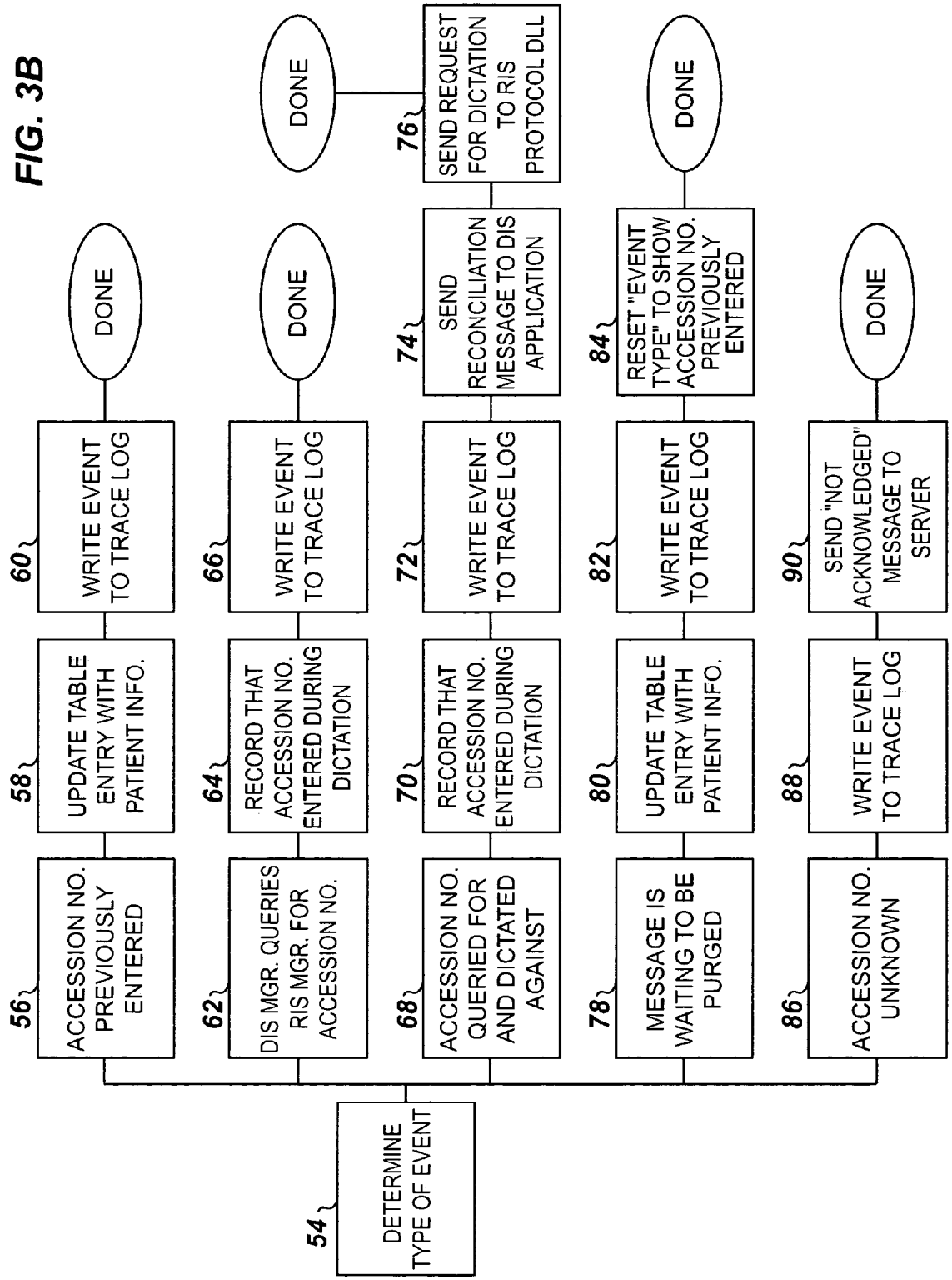

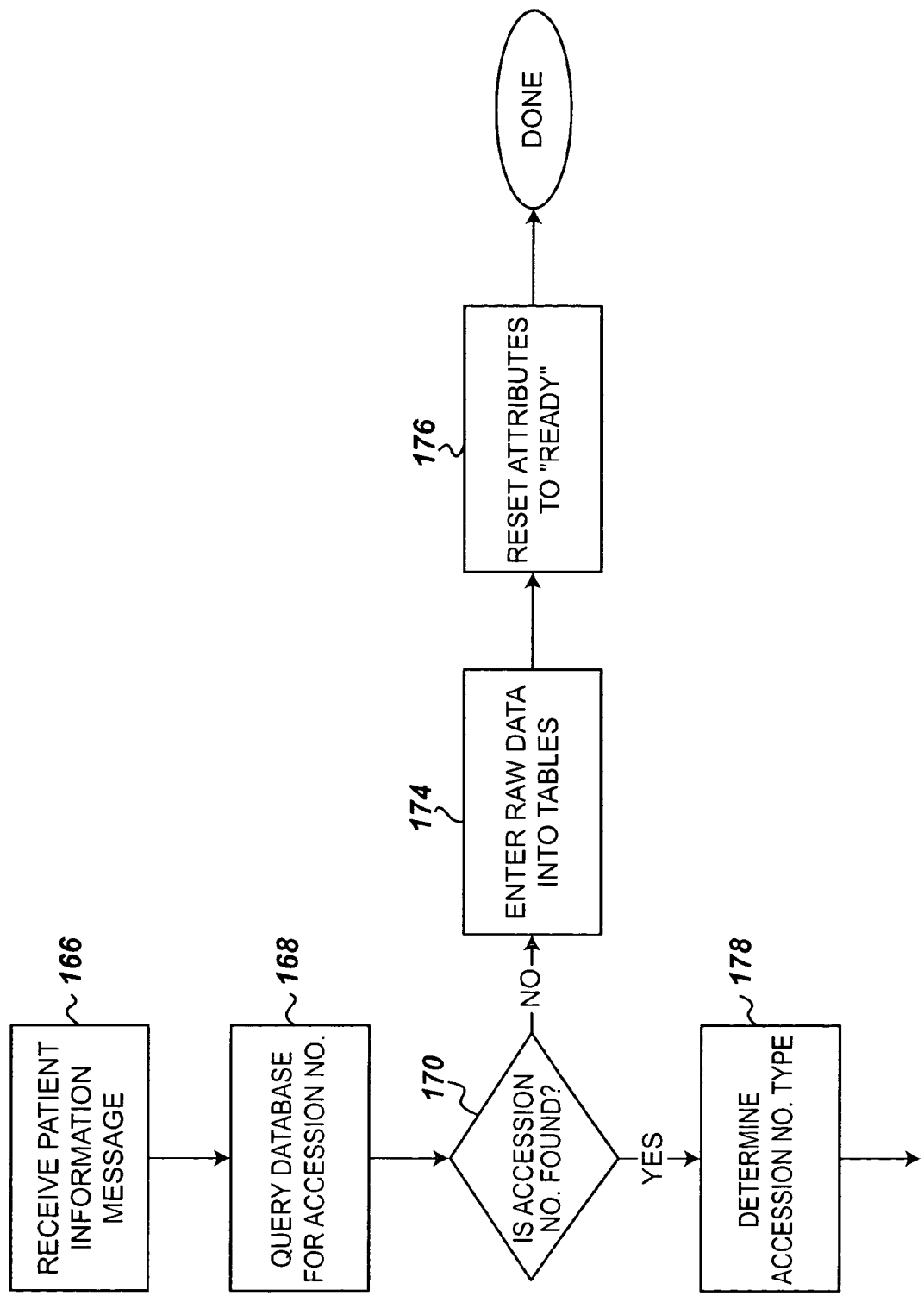

SYSTEM AND METHOD FOR INTERFACING A RADIOLOGY INFORMATION SYSTEM TO A CENTRAL DICTATION SYSTEM

FIELD OF THE INVENTION

The present invention relates to information systems and, more particularly, to an interface between information systems found within one organization and the storage capacities of such systems.

BACKGROUND OF THE INVENTION

Central dictation systems are well known and are a convenient and efficient way of arranging for the transcription of dictated information and producing corresponding documents in organizations that have numerous users who have need of transcription services. Central dictation systems are particularly common in hospitals and other large medical facilities, because the great value of the doctors' time requires that documentation be produced as efficiently as possible.

With central dictation systems, a user dictates data into an input station, whereby the voice message is transmitted to a central server, which assigns a job number and other identifying characteristics to the dictated information. Usually the user enters identifying information such as a user i.d. number, a file number, a patient number and so forth. This may be done via a keypad at the input station and/or by scanning a bar code with a bar code reading wand attached to the input station. The raw data is then transmitted to a dictation queue, where it awaits transcription. After the document is transcribed, a message is returned to the user reporting that the document has been completed and the number by which the document can be accessed.

Many hospitals also have a radiology information system. The function of a radiology information system is to keep track of x-ray examinations, CAT scans and other radiological procedures prescribed by attending physicians. After each procedure is complete, the resulting films or other images are reviewed by a radiologist, who dictates a report into the central dictation system. When the report is transcribed, the transcribed document is stored in the radiology information system and made available to the attending physician. The radiology information system assigns a transaction or "accession" number to each examination. The accession number is used to keep track of the x-rays themselves and the status of the examination and of the corresponding radiologist's report.

It has been known to provide a software interface between radiology information systems and central dictation systems to aid in transferring accession numbers and other information between the two systems. Other forms of cooperation between the two systems are also desirable. While the dictated report is in the queue awaiting transcription, the radiologist should be able to obtain information regarding its status, and should be able to dictate additional data regarding a particular patient under a new but related accession number. The radiologist should also be able to obtain information regarding the status of a document and related accession numbers.

Although the central dictation and radiology information systems function well independently, the current state of interfaces between the two systems leaves something to be desired. This is in part due to the limited storage capacity of the combined system.

It would be advantageous if the storage capacities of the central dictation system and radiology information system were increased.

It would also be desirable to improve error diagnosis features of software provided as an interface between the radiology information system and the dictation system.

Also, some radiology information systems disconnect from the interface at the end of each transaction. With known client-server socket protocols, this creates a large processing overhead for frequently instantiating and destroying server socket objects.

OBJECTS AND SUMMARY OF INVENTION

It is an object of the invention to provide a software interface between a radiology information system and the central dictation system so as to allow for an expanded data storage capacity.

It is a further object of the invention to provide a software interface between such systems in which more detailed diagnostic information is made available.

It is still a further object of the invention to increase the processing efficiency of such a software interface.

According to an aspect of the invention, a software system provides an interface between a radiology information system and a central dictation system, the software system including a first application module for exchanging data messages with the radiology information system, a second application module for exchanging data messages with the central dictation system and with the first application module; and a database management system, wherein the first application module includes procedures for accessing the database management system; and the second application module includes procedures for accessing the database management system.

According to further aspects of the invention, at least one of the first application module and the second application module programs a first server computer and the database management system programs a second server computer which is separate from, but interfaced to, the first server computer, wherein the first server computer includes a mass storage component in which the central dictation system stores voice files corresponding to dictation jobs. This permits storage of records related to many more accession numbers than has been possible in previous systems wherein central dictation systems had limited storage capabilities for accession numbers. The radiology information system may be maintained in a third server computer which is separate from the first and second servers but which is interfaced to the first server.

According to other aspects of the invention, the software system may include a first protocol DLL for transmitting data messages between the first application module and the central dictation system; a second protocol DLL; and a communication DLL for transmitting data messages between the second protocol DLL and the radiology information system; the second protocol DLL transmitting messages between the second application module and the communication DLL.

According to another aspect of the invention, a central dictation system is interfaced to a radiology information system by a method which includes the steps of providing a first application module for exchanging data messages with the radiology information system; providing a second application module for exchanging data messages with the central dictation system and with the first application module; providing a database management system; transmitting queries from said first application module to said database management system; and transmitting queries from said second application module to said database management system.

According to yet another aspect of the invention, a software system includes multiple software modules, wherein a respective trace buffer is provided for each of said software modules, each trace buffer for storing a plurality of records and maintained in RAM and configured as a ring buffer, each of said records indicative of an instruction executed by the respective software module, wherein the respective contents of each trace buffer are dumped to a nonvolatile storage device in response to occurrence of an event in any one of the software modules. This aspect of the invention provides for more detailed and extensive information to be made available for diagnostic analysis in the event of a system failure.

According to still another aspect of the invention, there is provided a method of managing a software system in which messages are passed between a first process and a second process by means of a server socket in the first process and a client socket in the second process, the client socket for sending said messages and the server socket for receiving said messages, the method including the steps of: registering the server socket in the first process; instantiating the server socket in the first process; placing the server socket into an accept mode in which the server socket awaits initiation of communication by the client socket; and placing the server socket into a receive mode upon initiation of communication by the client socket, the server socket receiving at least one message from the client socket in the receive mode; wherein the server socket is maintained in existence and placed in the accept mode upon the client socket terminating communication with the server socket. This aspect of the invention increases processing efficiency in certain circumstances, particularly when the process which maintains the client socket frequently interrupts communication with the process which maintains the server socket.

Other objects, features and advantages of the present invention will become apparent from the subsequent more detailed description of preferred embodiments.

BRIEF DESCRIPTION OF THE DRAWINGS

FIGS. 3A and 3B illustrate in the form of a flow-chart a process according to which a radiology information system manager application module shown in FIG. 2 identifies the accession numbers for documents.

FIGS. 7A and 7B illustrate in the form of a flow-chart a process according to which a dictation information system manager application module shown in FIG. 2 identifies the accession numbers for documents.

DESCRIPTION OF PREFERRED EMBODIMENTS

System Overview

Figure 1:
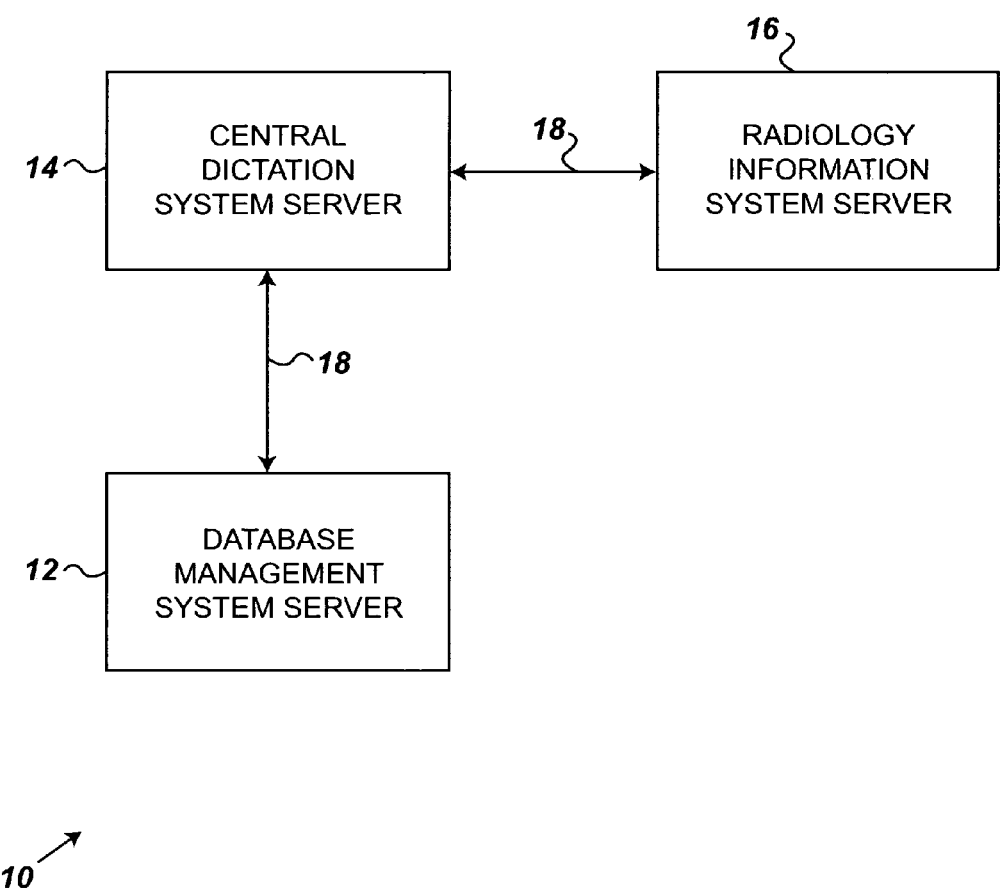
FIG. 1 is a block diagram representation of an information system in which the present invention is applied.

A preferred embodiment of the invention will now be described, initially with reference to FIG. 1. In FIG. 1, reference numeral 10 generally indicates the hardware aspects of an information system in which the invention may be applied. The major components of the central dictation system 10 are a database management system server computer 12, a central dictation system server computer 14, a radiology information system server computer 16, and a communications network 18 that connects the central dictation system server 14 and the radiology information system server 16, and the central dictation system server 14 and the database management system server 12.

All of the components shown in FIG. 1 may be constituted by standard hardware. Preferably the communication network 18 is a conventional local area network (LAN) and the servers 12, 14, 16 are conventional computing devices.

Figure 2:
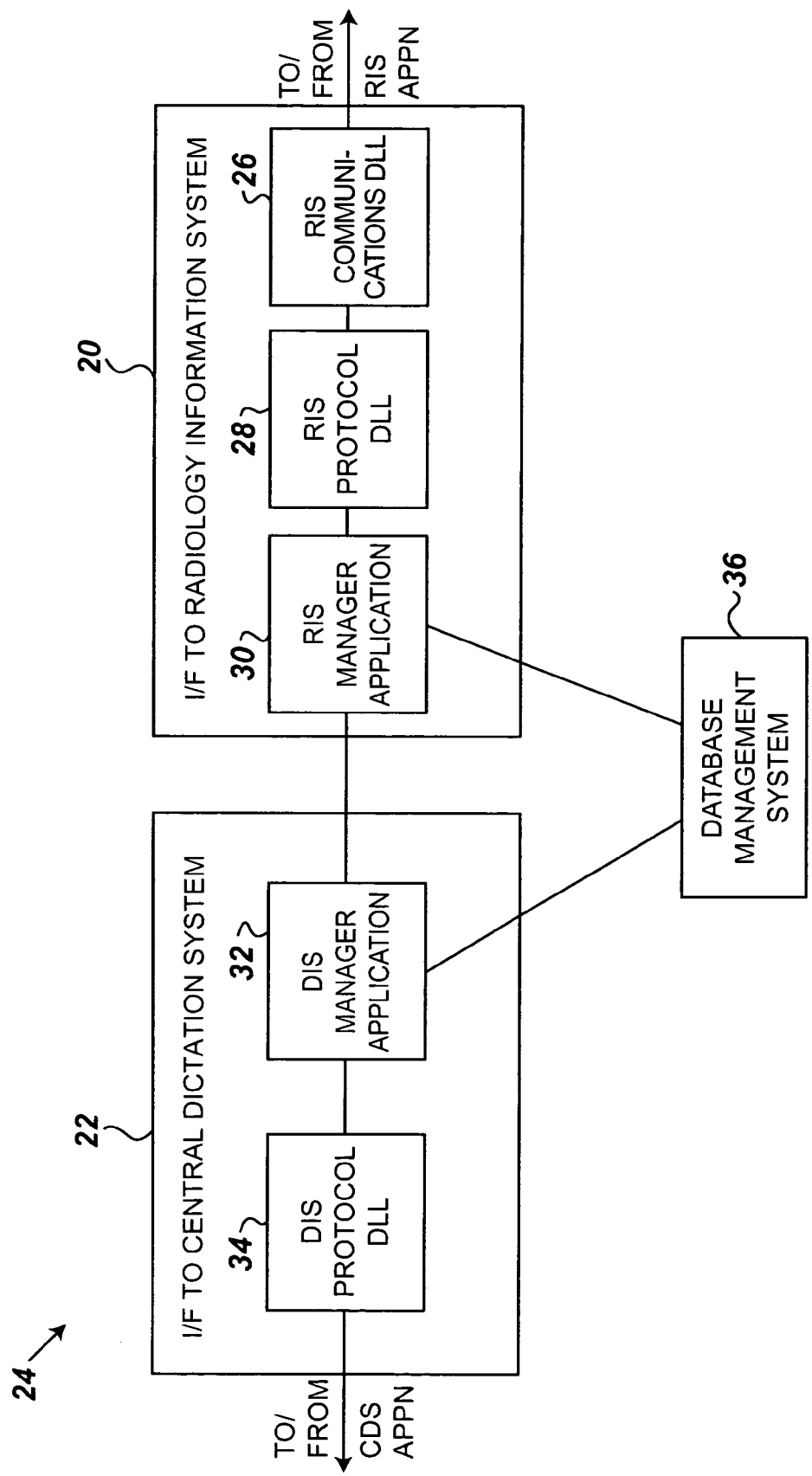
FIG. 2 is a functional block diagram showing software which provides an interface in accordance with the invention between the radiology information system and central dictation system shown in FIG. 1.

FIG. 2 is a block diagram showing interface software modules provided in accordance with the invention. This software may be resident in the central dictation system server 14 shown in FIG. 1. Alternatively, the interface software may be resident on a separate computer (not shown) connected for data communication with each of the servers 12, 14, 16. As other alternatives, the interface software may be resident on the DBMS server 12 or the RIS server 16 (in which cases a data communication path should be provided between DBMS server 12 and RIS server 16). It is also contemplated to divide the interface software between two or more computers. Furthermore, all of the functions of the system shown in FIG. 1 may be consolidated in a single server, or the functions of any two of the three servers may be combined in one server.

Interface Software Modules

The software illustrated in FIG. 2 is generally indicated by reference numeral 24, and provides an interface between the application software which controls the central dictation system and the application software which controls the radiology information system. Both of these applications may be conventional. The interface software 24 is made up of a radiology information system interface portion 20 and a central dictation system interface portion 22. The radiology information system interface portion 20 contains three components, namely a communications dynamic linked library (DLL) 26, a protocol DLL 28, and a manager application 30. The comm. DLL 26 unpacks from the communication system format messages received from the radiology information system (RIS). The comm. DLL also translates into the communication systems format messages to be sent to the RIS. The protocol DLL 28 converts messages between a raw data format and a format prescribed by a messaging protocol used by the RIS.

The manager application 30 handles messages and exchanges information with the central dictation system interface portion 22. Functions performed by the manager application 30 will be described in greater detail below.

The central dictation system interface portion 22 includes two components: a protocol DLL 34 and a manager application 32. No comm. DLL is required in the interface portion 22 so long as the interface software 24 is resident in the same computer with the central dictation system.

The protocol DLL 34 of the dictation system interface portion 22 converts messages between a raw data format and a format prescribed by a messaging protocol used by the central dictation system. The manager application 32 of the dictation system interface portion 22 handles messages and exchanges information with the RIS interface portion 20. Functions performed by the application 32 will be described in more detail below.

Both the radiology information system interface portion 20 (particularly application 30) and the central dictation system interface portion 22 (particularly application 32) are in communication with the database management system 36. The DBMS 36 stores information relating to radiological examinations and related reports processed through the RIS and the central dictation system. The database management system 36 is preferably resident on its own server 12 (FIG. 1), so that it has a storage capacity that is theoretically unlimited. In practice, of course, the storage capacity of the DBMS 36 is limited to that of the server 12 and any associated memory units.

FIGS. 3A and 3B illustrate in the form of a flowchart processes carried out by the radiology information system manager application module 30. In an initial step 40 of FIG. 3A, the radiology information system manager application module 30 receives patient information in the form of a message passed from the radiology information system. The radiology information system manager application module 30 then sends a query (indicated at step 42) to the database management system 36 regarding whether corresponding patient information, including an accession number, exists within the system. The database 36 is examined for a matching accession number (step 44). If a matching accession number is not found, the information from the message is stored to data tables, as indicated at step 46, and the application resets itself to a ready condition (step 48).

If a matching accession number is found at step 44, the application determines the type of the accession number, as indicated by step 52, and takes appropriate action.

FIG. 3B illustrates an event handling routine carried out by the manager application 30. Initially, as indicated at step 54, the application determines what kind of event has occurred. If the accession number has been previously entered (step 56), the data table is updated with the patient's new information (step 58) and the event is written to the trace log (step 60).

If an accession number was not previously entered and has not been queried for, the radiology information system manager application queries for the accession number (step 62), the system records that an accession number was entered during dictation (step 64), and the event is written to the trace log (step 66).

If an accession number has been queried for and dictated against (step 68), the RIS manager application records that an accession number was entered during dictation (step 70) and writes the event to the trace log (step 72). The application also sends a reconciliation message to the dictation information system manager application 32 (step 74), and finally sends a request for dictation to the radiology information system protocol DLL 28 (step 76).

In the event a message is obsolete and waiting to be purged, as indicated at step 78, the RIS manager application 30 updates the data table entry with all relevant patient information (step 80), writes the event to the trace log (step 82), and sends a new message indicating that an accession number had been previously entered (step 84).

Finally, if the application cannot locate a matching accession number (step 86), it writes the event to the trace log (step 88) and then issues an error message (step 90).

Figure 4A:
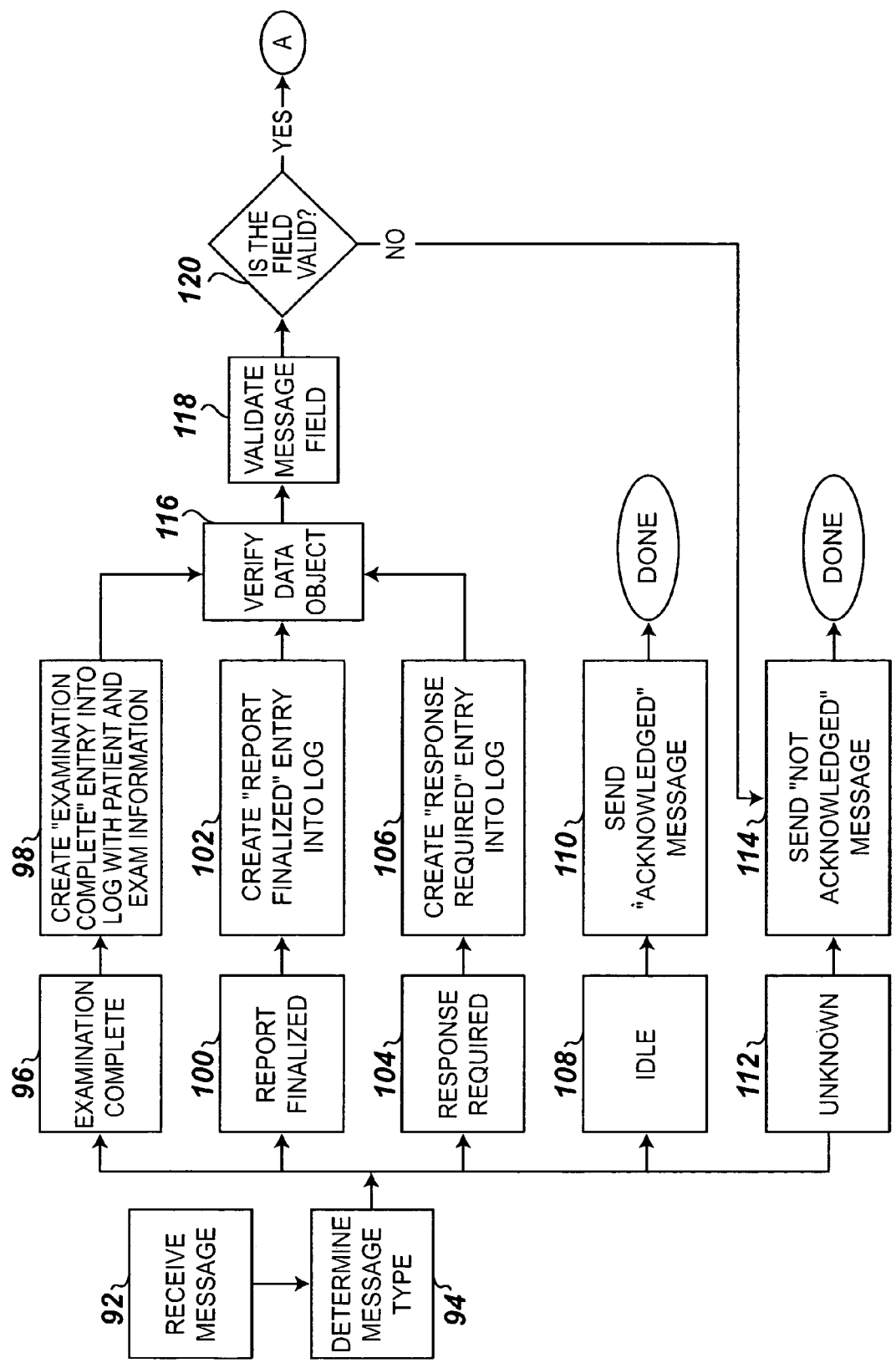
FIGS. 4A and 4B illustrate in the form of a flow-chart a method by which a radiology information system protocol DLL module shown in FIG. 2 handles data objects.
Figure 4B:
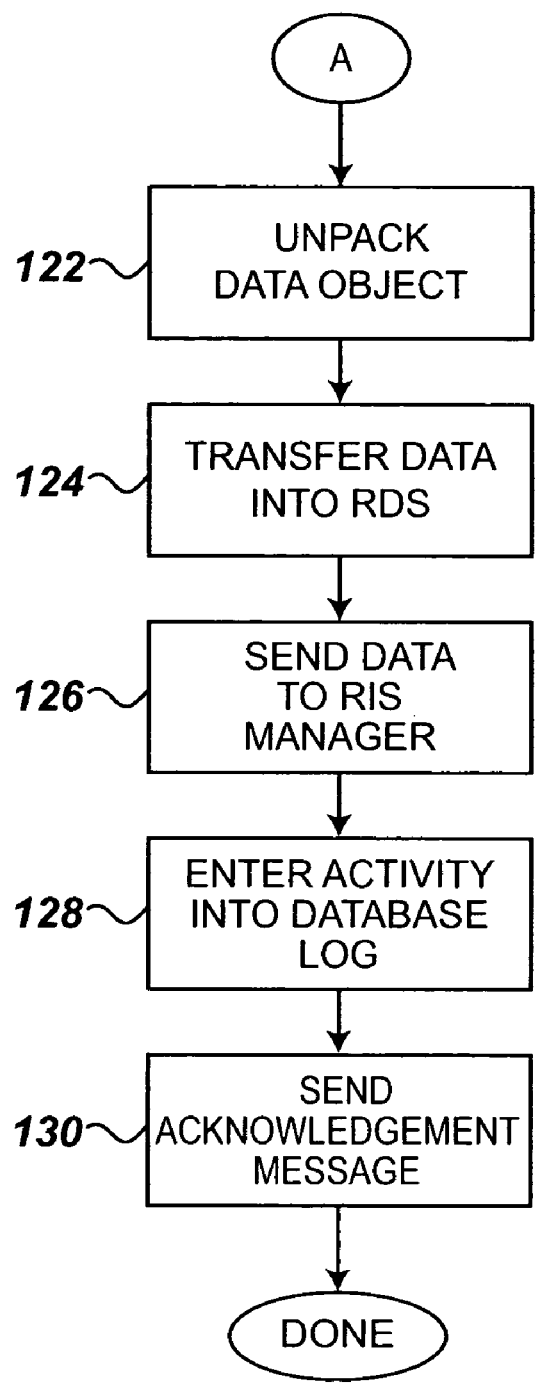

FIGS. 4A and 4B illustrate in the form of a flowchart a process by which the radiology information system protocol DLL 28 handles data objects. Once the radiology information system DLL receives a message (step 92), it determines the message type (step 94). If it cannot identify the message (step 112), it issues an error message (step 114). If the message indicates an idle condition (step 108), the DLL simply acknowledges the message (step 110).

With regard to three types of messages, the radiology information system protocol DLL 28 must verify the format of the data object, as indicated at step 116. This occurs in the event of the type of message indicating that an examination has been completed (step 96), in which case an "examination complete" entry is made in the log with patient and exam information (step 98); or in the event of a "report finalized" message (step 100), the event is logged (step 102), or if the message requires a response (step 104), a "response required" entry is made in the log (step 106).

Once the format of the data object has been verified at step 116, the radiology information system protocol DLL 28 validates the message field (step 118). If the field is found not to be valid at step 120, the DLL returns an error message (step 114). If the field is valid, the radiology information system DLL 28 proceeds to handle the data object as illustrated in FIG. 4B.

Initially, the DLL unpacks the data object, as indicated at step 122. It then converts the data to a raw data string (step 124), and sends the raw data to the radiology information system manager application 30 (step 126). Thereafter, the DLL logs the activity (step 128) and sends an acknowledgement message to the RIS (step 130).

Figure 5:
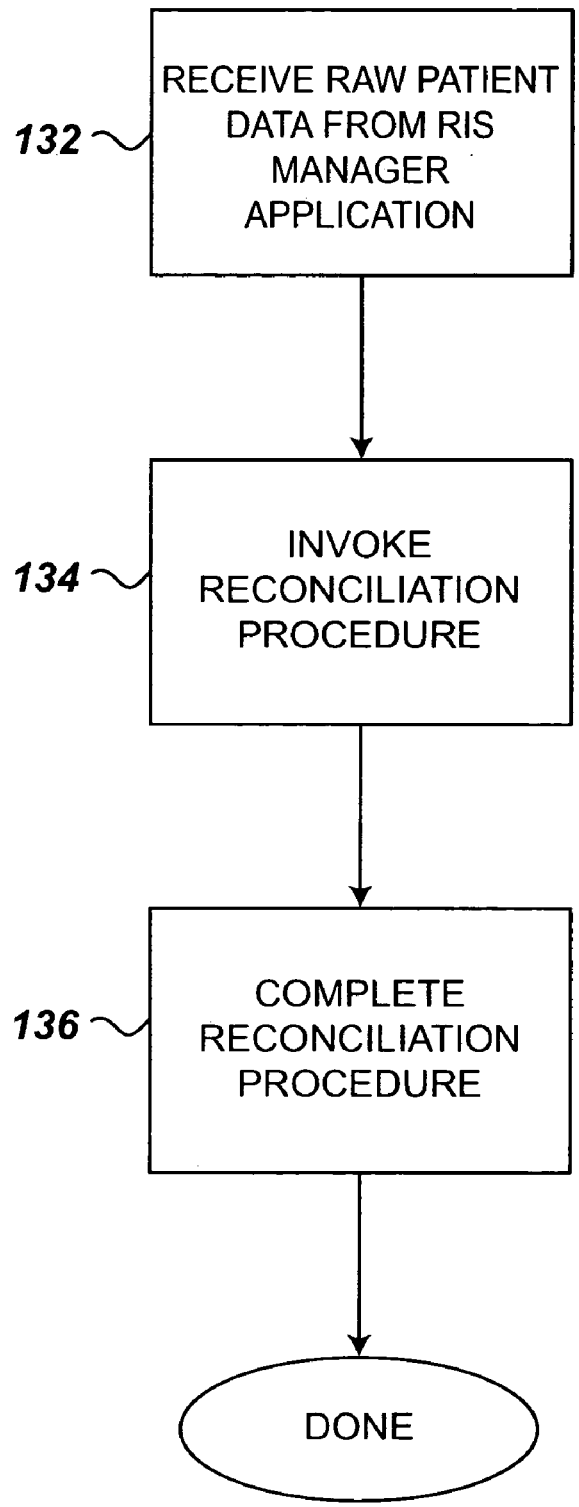
FIG. 5 is a flow-chart illustration of how a dictation information system manager application module shown in FIG. 2 reconciles data received from the radiology information system.

FIG. 5 is a flow-chart illustration of how the dictation information system manager application module 32 as shown in FIG. 2 reconciles data received from the radiology information system interface portion 20. As step 132, the dictation information system manager application module 32 receives raw patient data from the radiology information system manager application 30. A reconciliation procedure is then invoked at step 134 and determined to be complete at step 136.

Figure 6A:
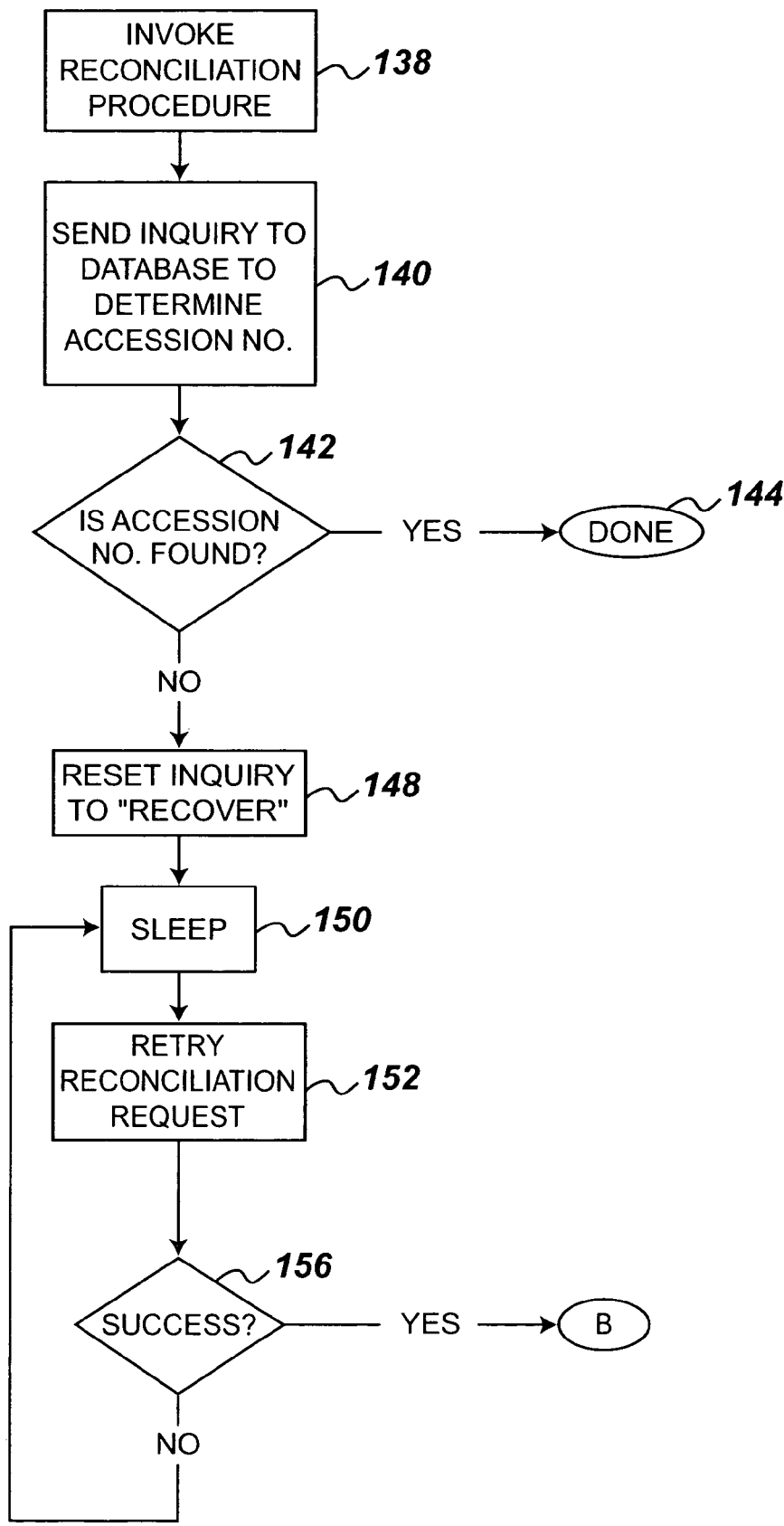
FIGS. 6A and 6B are a flow-chart illustration showing details of a reconciliation procedure.
Figure 6B:
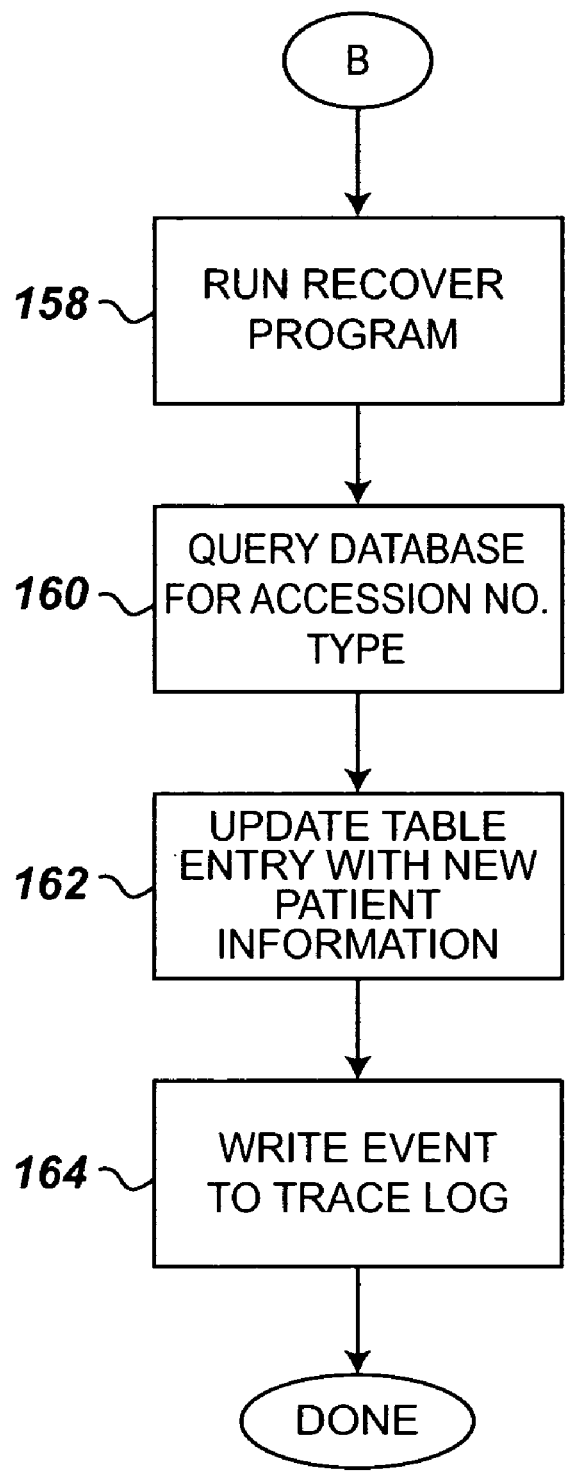

FIGS. 6A and 6B together form a flow-chart illustration of some details of the reconciliation procedure. Step 138 indicates invocation of the reconciliation procedure. The manager application then sends an inquiry to the database 36 to determine the accession number which corresponds to the patient information (step 140). If the accession number is found (step 142), the reconciliation procedure is complete (step 144).

If the accession number is not found at step 142, a recovery routine is invoked at step 148. After a pause 150, the application retries the reconciliation request (step 152). If such request is found to be unsuccessful at step 156, the routine loops back to step 150. If the reconciliation request is found to be successful at step 156, the system runs a recover program (step 158, FIG. 6B). The database 36 is then queried for the accession number (step 160). Next the table entry is updated with new patient information (step 162) and the event is written to the trace log (step 164).

Figure 7B:
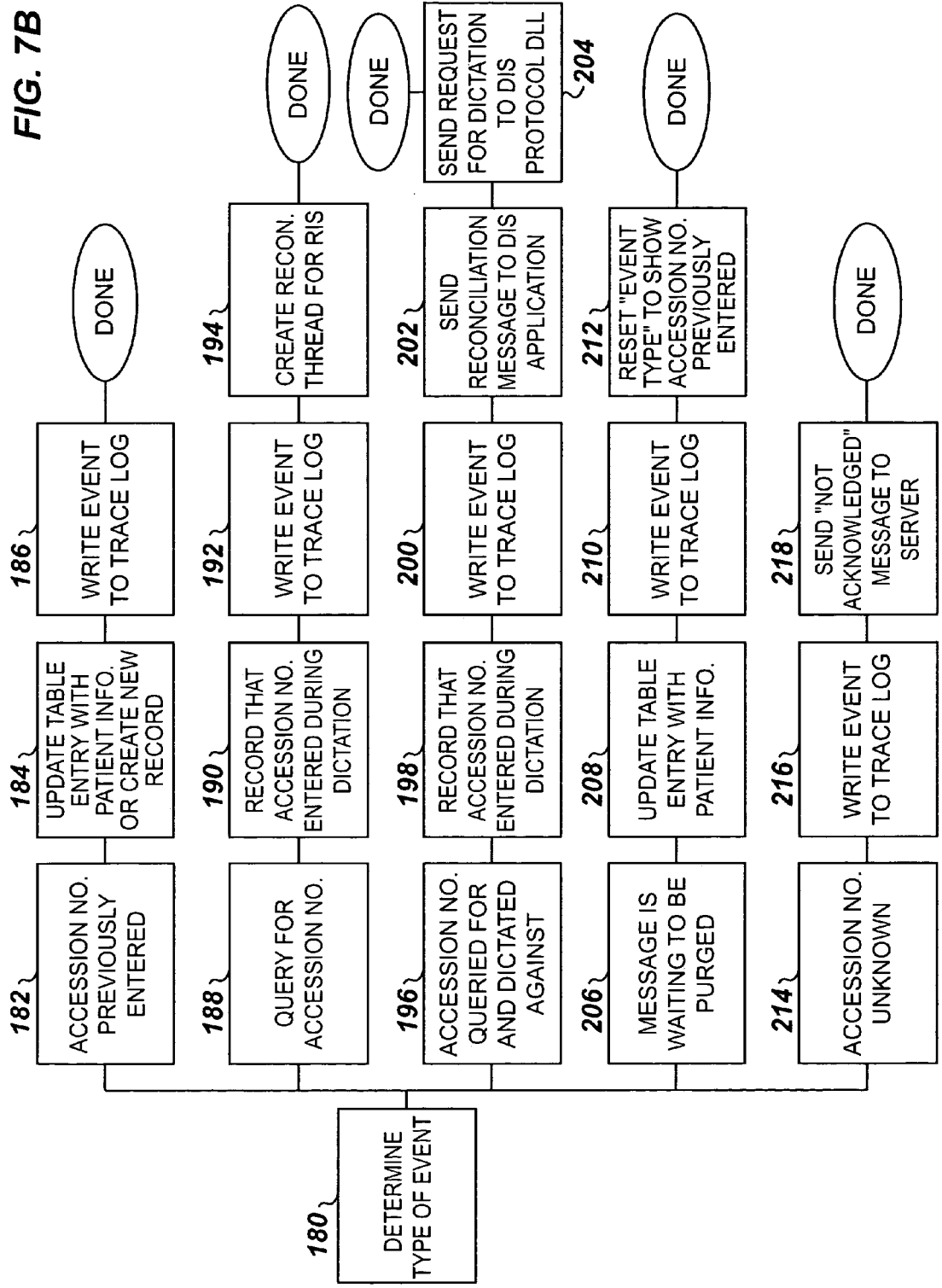

FIGS. 7A and 7B illustrate in the form of a flow-chart a process according to which the dictation information system manager application module 32 identifies relevant existing information, such as accession numbers, for dictated documents. In an initial step 166 of FIG. 7A, the dictation information system manager application module 32 receives patient information in the form of a message from the dictation system. The dictation information system manager application module 32 then sends a query (step 168) to the database management system 36 regarding whether a corresponding accession number exists within the system. If a matching accession number is not found at step 170, the raw information is stored to data tables (step 174) and the application resets itself to a ready condition (step 176).

If a matching accession number is found at step 170, the application determines the type of the accession number (step 178) and takes appropriate action. FIG. 7B illustrates an event handling routine carried out by the manager application 32. Initially as indicated at step 180, the application determines what kind of event has occurred. If the accession number has been previously entered (step 182), the data table is updated with the patient's new information (step 184) and the event is written to the trace log (step 186).

If an accession number was not previously entered and has not been queried for, the dictation system manager application 32 queries for a matching accession number (step 188), the system records that an accession number was entered during dictation (step 190), the event is written to the trace log (step 192), and a reconciliation message is sent to the radiology information system (step 194).

If an accession number has been queried for and dictated against (step 196), the manager application 32 records that an accession number was entered during dictation (step 198), and writes the event to the trace log (step 200). The manager application 32 also sends a reconciliation message to the dictation information system application (step 202), and finally sends a request for dictation to the dictation information system protocol DLL 34 (step 204).

In the event a message is obsolete and waiting to be purged, as indicated at step 206, manager application 32 updates the data table entry with all relevant patient information (step 208), writes the event to the trace log (step 210), and sends a message indicating that an accession number had been previously entered (step 212).

Finally, if the application cannot locate a matching accession number (step 214), it writes the event to the trace log (step 216) and then issues an error message (step 218).

Trace Buffers

Figure 8:
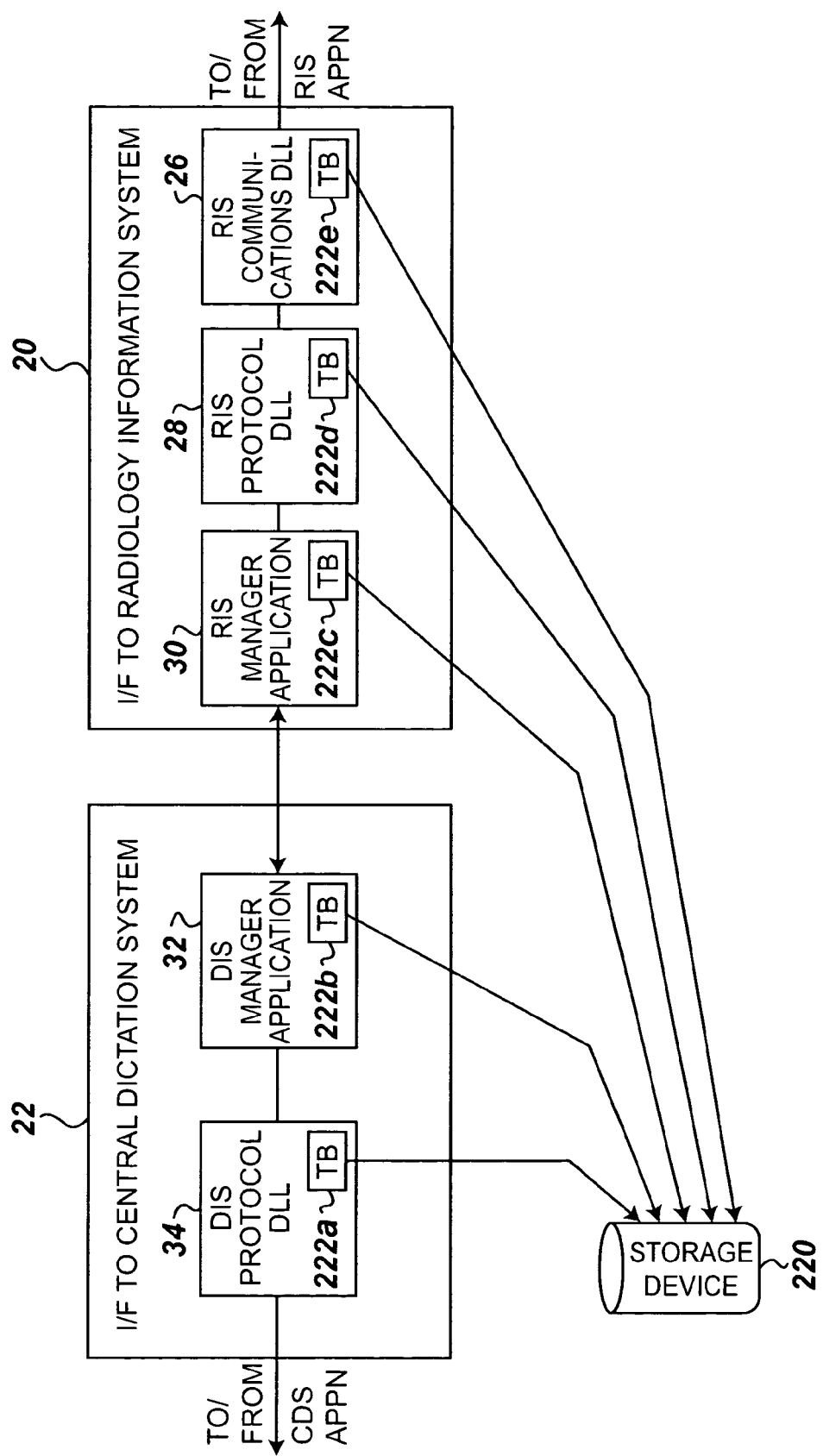
FIG. 8 is a block diagram showing trace buffers maintained by the software modules of FIG. 2 in accordance with the invention.

FIG. 8 schematically illustrates another aspect of the invention. According to this aspect, respective trace buffers 222a–222e are maintained by each of the software components shown in FIG. 8 (and FIG. 2), namely the radiology information system communications DLL 26, the radiology information system protocol DLL 28, the radiology information system manager application 30, the dictation information system manager application 32, and the dictation information system protocol DLL 34, respectively. It is contemplated that the trace buffers be maintained in RAM.

Figure 9:
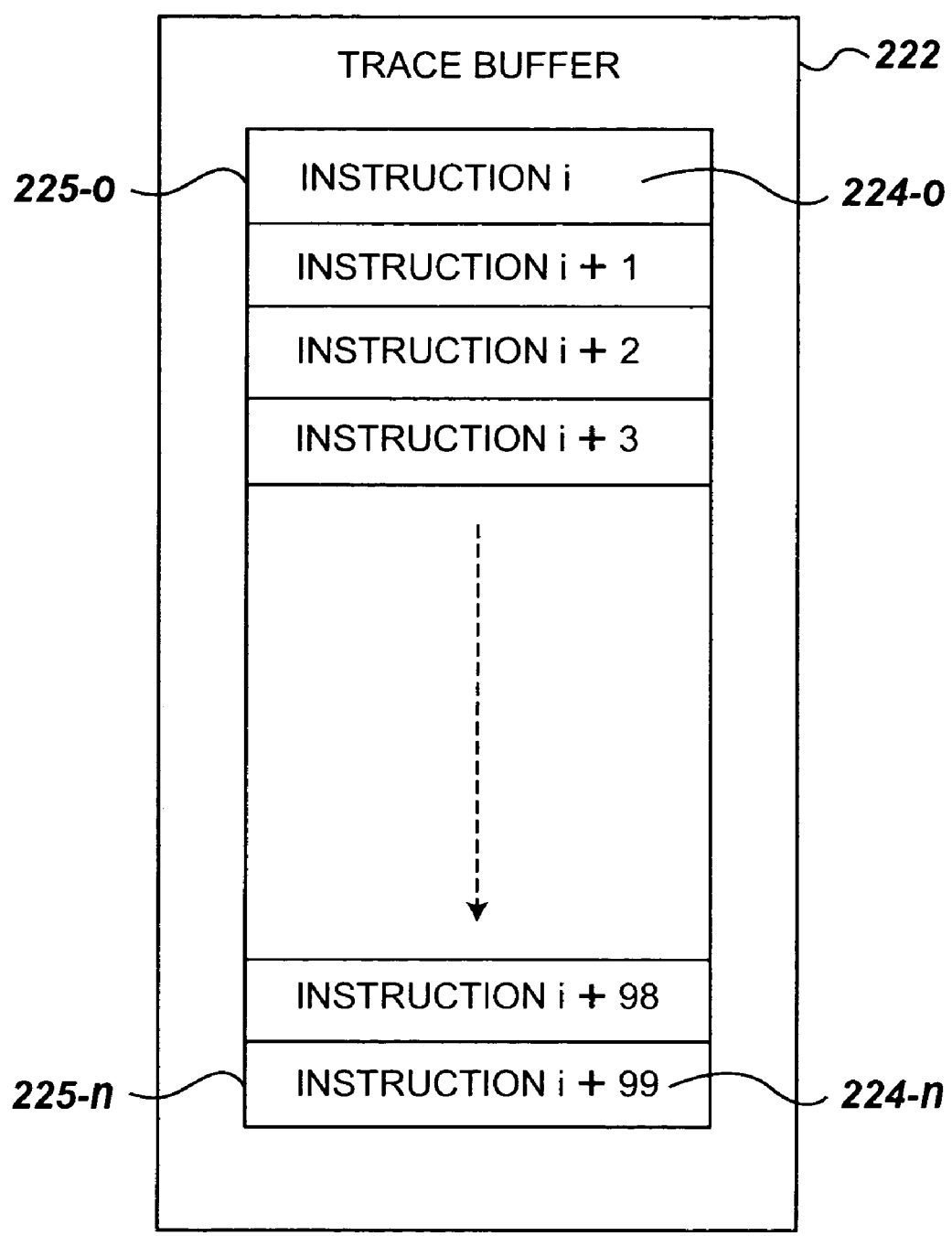
FIG. 9 is a block diagram representation of a typical one of the trace buffers of FIG. 8.

A typical one of the trace buffers is schematically illustrated in FIG. 9. As shown in FIG. 9, each trace buffer 222 is preferably configured as a ring buffer which can store a plurality of records 224-0 to 224-n in respective storage locations 225-0 to 225-n. In a preferred embodiment the number of storage locations is 100 in each buffer, but of course the number of storage locations provided may be more or less than 100. Since the trace buffer is a ring buffer, when all the storage locations are full, the next record to be stored replaces the oldest record in the buffer.

Figure 10:
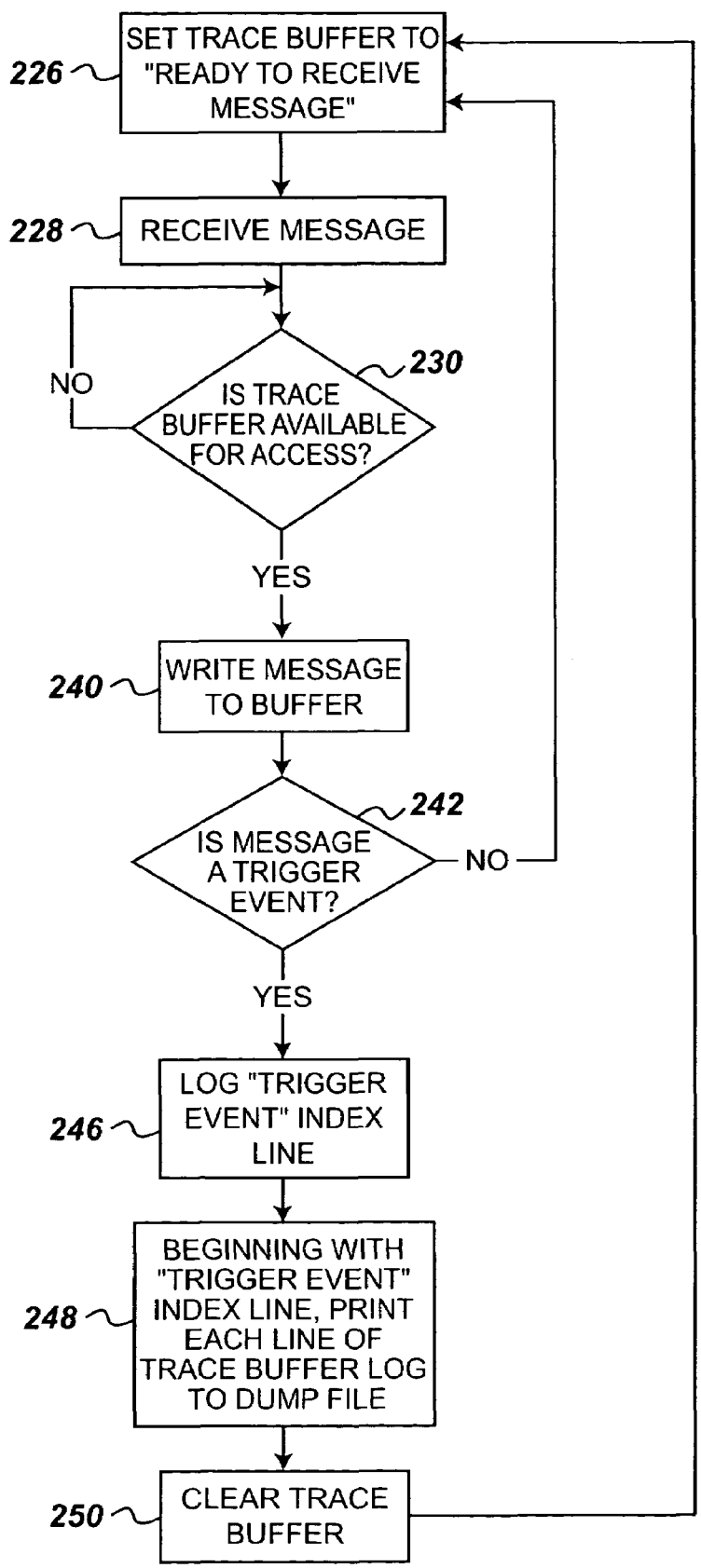
FIG. 10 illustrates in the form of a flow chart a trace buffer life cycle.

FIG. 10 illustrates the life cycle of one of the trace buffers 222. A trace buffer is initialized (step 226) to a condition in which it is ready to store data. A message to be stored in the trace buffer is received (step 228) and it is then determined, at step 230, whether the trace buffer is available for access. If so, the message is written into the next storage location in the buffer (step 240). Otherwise, the routine idles until access to the trace buffer is allowed.

After step 240, it is determined, at step 242, whether the message represents an event which should trigger permanent storage of the trace buffer. If not, the buffer is returned to the ready condition.

However, if it was found at step 242 that the message was indicative of a trigger event, then step 246 follows. (Examples of trigger events are a system failure, a fatal error in the software component which maintains the trace buffer, or a fatal error in another one of the software components.) At step 246 the trigger event is logged to an index line. Then, the contents of the entire log of the trace buffer are dumped (step 248) to a nonvolatile storage device 220 (FIG. 8). The nonvolatile storage device 220 may be, for example, a hard disk.

The trace buffer is then cleared (step 250), and the trace buffer is reinitialized.

Figure 11:
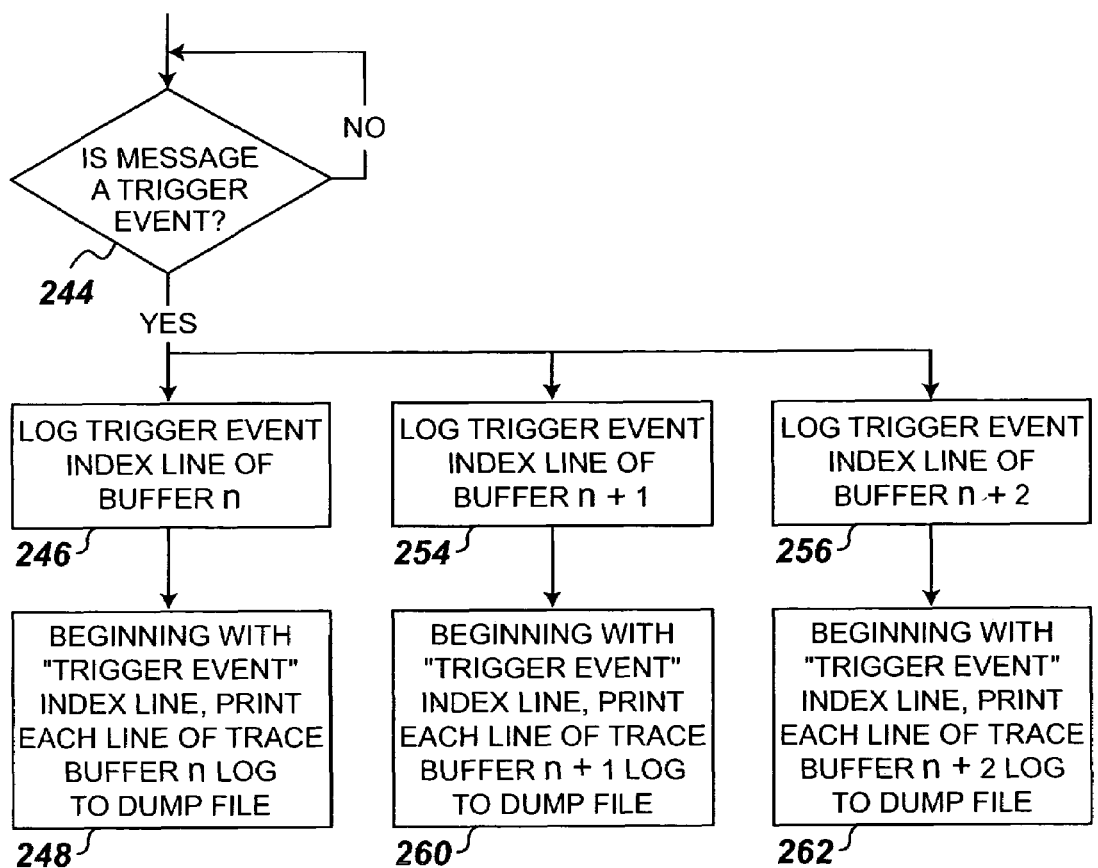
FIG. 11 illustrates in the form of a flow chart dumping of all information from all trace buffers into a permanent storage device upon the occurrence of a trigger event.

FIG. 11 portrays, in flow chart form, further events that occur after a trigger event is logged to any one of the trace buffers 222a–222e. As seen from FIG. 11, it is determined at step 244 whether a trigger event has occurred. If so the trigger event is logged in an index line of each of the trace buffers of the respective software components (steps 246, 254, 256) and then the contents of the trace buffers are dumped to nonvolatile store 220 (steps 248, 260, 262).

In accordance with this aspect of the invention, a respective trace buffer is maintained by each one of several individual software components, and a trigger event which originates in any one of the software components, triggers a buffer dump from all of the components. Consequently, enhanced and more comprehensive diagnostic procedures are possible, since the activities of each component are stored for later analysis.

Socket Management

Figure 12:
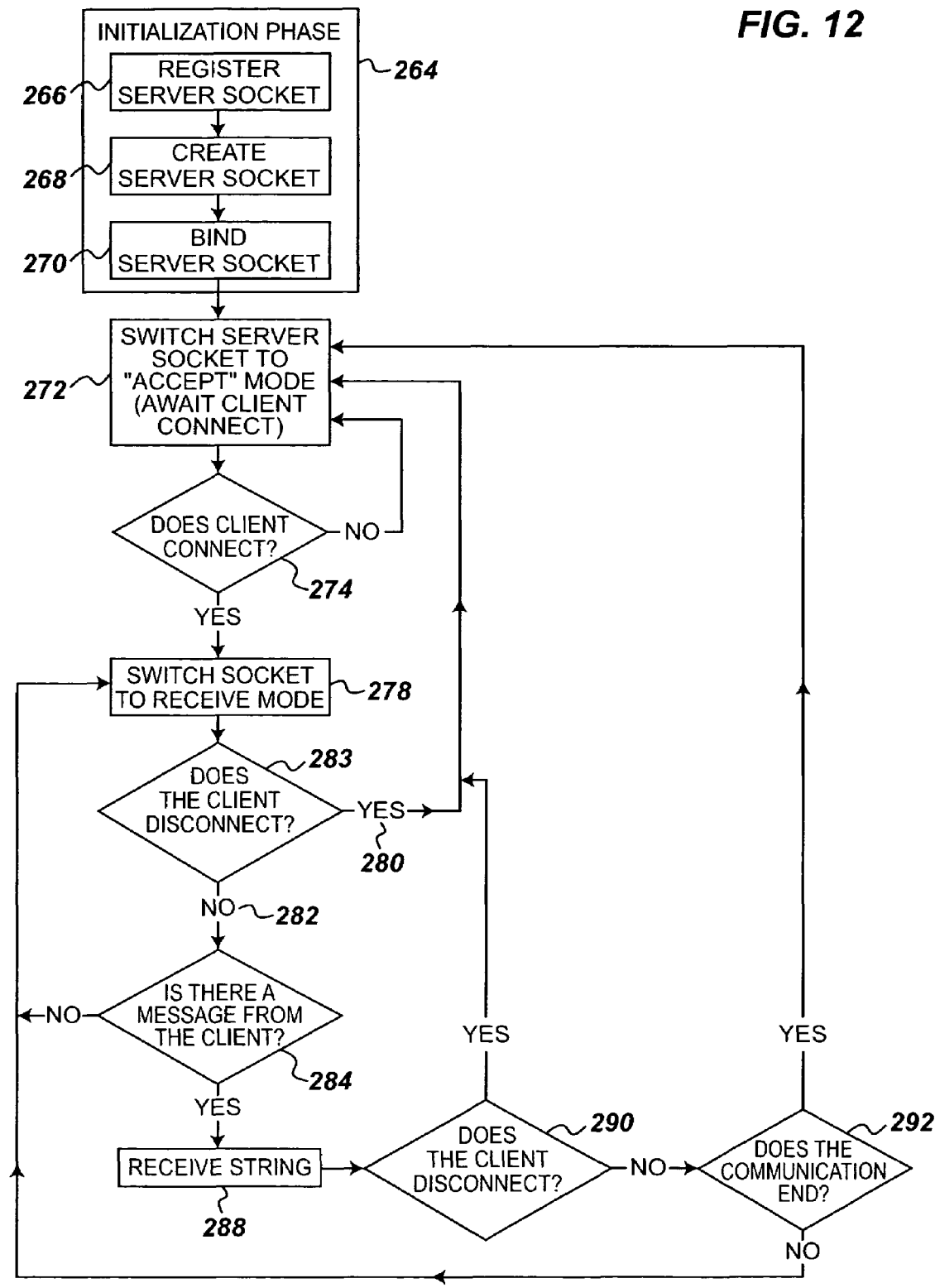
FIG. 12 illustrates in the form of a flow chart a process for managing a socket object in accordance with the invention.

FIG. 12 illustrates another aspect of the invention. According to this aspect, the overhead processing required for implementing a client-server socket model is reduced for certain environments in which the interface software of the present invention may be used.

In FIG. 12, block 264 as a whole represents an initialization phase for a server socket object. In accordance with conventional practice (as embodied, for example, in the Windows NT operating system), initialization includes the steps of registering a server socket object (step 266), creating or instantiating the server socket object (step 268) and binding the server socket object (step 270). Then, also according to known procedures, the server socket is placed in an "accept" mode (step 272), indicating that the socket is awaiting connection from a client socket.

The procedure of FIG. 12 idles, as indicated at block 274, until the client socket initiates communication. Once communication is initiated, the server socket is placed in a "receive" mode (step 278), wherein the server socket is enabled to receive information from the client. If the client disconnects (branch 280), the server socket is returned to the "accept" mode of step 272. If the client does not disconnect (branch 282), but there is no message from the client, the server socket idles in a loop made up of blocks 278, 283, 284.

If at block 284 a message is received from the client, the server socket receives and processes the message string (step 288). Once the string has been received and processed at block 288, it is determined once again whether the client has disconnected (step 290) or if the communication is broken (step 292). If either one of these occurs, the server socket is returned to the accept mode of block 272. Otherwise the socket continues in the receive mode of block 278.

The procedure described above in connection with FIG. 12 departs from the conventional practice for client/server sockets in that the server socket is maintained in existence and returned to an accept mode when the client socket disconnects or the physical communication channel is shut down or disrupted. By contrast, conventional practice calls for the server socket to be eliminated (de-instantiated) upon the occurrence of either of these two events. The present inventors have found that the conventional practice results in an undesirable amount of processing overhead, including frequent destruction and instantiation of server socket objects, in cases where the RIS to which the interface is made frequently disconnects from the interface software or the communication channel frequently shuts down. For example, some RIS software is arranged to disconnect from the server socket in the interface after each transaction. Since the number of transactions per day may be in the thousands, the improved procedure of the present invention may substantially reduce the processing burden by maintaining the server socket in existence even after the client has disconnected.

It is to be understood that the above description may indicate to those skilled in the art additional ways in which the principles of this invention may be used without departing from the spirit of the invention. The particularly preferred embodiments of the apparatus are thus intended in an illustrative and not limiting sense. The true spirit and scope of the invention are set forth in the following claims.

What is claimed is:

1. A method of interfacing a central dictation system to a radiology information system with a software system, the method comprising the steps of:
   providing a first application module configured to interface with the radiology information system and a database management system;
   providing a second application module configured to interface with the central dictation system, the first application module, and the database management system, the central dictation system having a dictation server;
   receiving data from the radiology information system through the first application module at the second application module;
   receiving patient information from the radiology information system at the first application module;
   transmitting a query based on the patient information to the database management system from a first manager application module of the first application module;
   determining a status of a record for the patient information in the database management system;
   determining a type of event based on the patient information in response to determination of the status being existent for the record;
   determining a status of an accession number associated with the patient formation;
   updating the database management system with the patient information in response to a determination of the status being existent for the accession number; and
   writing the type of event to a trace log.

2. The method according to claim 1, further comprising the steps of:
   determining a status of an accession number in the database management system;
   determining whether a query has been issued for the accession number in the database management system; and
   querying for the accession number in the database management system in response to determination of non-existence status for the accession number and no query being issued for the accession number.

3. The method according to claim 2, further comprising the steps of writing the accession number in the database management system from a dictation and writing the type of event to a trace log.

4. The method according to claim 3, further comprising the step of transmitting a reconciliation message to a manager application module of said first application module.

* * * * *